US012227791B2

(12) United States Patent
Sanches-Kuiper et al.

(10) Patent No.: US 12,227,791 B2
(45) Date of Patent: *Feb. 18, 2025

(54) METHODS AND COMPOSITIONS FOR PREPARING NUCLEIC ACID LIBRARIES

(71) Applicant: ILLUMINA, INC., San Diego, CA (US)

(72) Inventors: Raquel Maria Sanches-Kuiper, Little Chesterford (GB); Vincent Peter Smith, Little Chesterford (GB); Sean Humphray, Little Chesterford (GB)

(73) Assignee: Illumina, Inc., San Diego, CA (US)

( * ) Notice: Subject to any disclaimer, the term of this patent is extended or adjusted under 35 U.S.C. 154(b) by 158 days.

This patent is subject to a terminal disclaimer.

(21) Appl. No.: 18/051,836

(22) Filed: Nov. 1, 2022

(65) Prior Publication Data

US 2023/0272453 A1 Aug. 31, 2023

Related U.S. Application Data

(63) Continuation of application No. 17/068,062, filed on Oct. 12, 2020, now Pat. No. 11,512,340, which is a continuation of application No. 16/703,527, filed on Dec. 4, 2019, now Pat. No. 10,988,797, which is a continuation of application No. 16/372,793, filed on Apr. 2, 2019, now Pat. No. 10,683,532, which is a continuation of application No. 15/029,103, filed as application No. PCT/US2014/060942 on Oct. 16, 2014, now Pat. No. 10,294,511.

(60) Provisional application No. 61/914,204, filed on Dec. 10, 2013, provisional application No. 61/892,220, filed on Oct. 17, 2013.

(51) Int. Cl.
C12Q 1/6806 (2018.01)
C12N 15/10 (2006.01)

(52) U.S. Cl.
CPC ....... *C12Q 1/6806* (2013.01); *C12N 15/1093* (2013.01)

(58) Field of Classification Search
CPC ............ C12Q 1/6806; C12Q 2523/303; C12N 15/1093
See application file for complete search history.

(56) References Cited

U.S. PATENT DOCUMENTS

| | | |
|---|---|---|
| 5,695,934 A | 12/1997 | Brenner |
| 5,714,330 A | 2/1998 | Brenner |
| 5,750,341 A | 5/1998 | Macevicz |
| 5,912,148 A | 6/1999 | Eggerding |
| 6,130,073 A | 10/2000 | Eggerding |
| 6,210,891 B1 | 4/2001 | Nyren |
| 6,258,568 B1 | 7/2001 | Nyren |
| 6,306,597 B1 | 10/2001 | Macevicz |
| 6,432,360 B1 | 8/2002 | Church |
| 6,485,944 B1 | 11/2002 | Church |
| 6,511,803 B1 | 1/2003 | Church |
| 6,787,308 B2 | 9/2004 | Balasubramanian |
| 6,833,246 B2 | 12/2004 | Balasubramanian |
| 6,969,488 B2 | 11/2005 | Bridgham |
| 7,115,400 B1 | 10/2006 | Adessi |
| 2005/0064460 A1 | 3/2005 | Holliger |
| 2005/0130173 A1 | 6/2005 | Leamon |
| 2007/0099208 A1 | 5/2007 | Drmanac |
| 2009/0026082 A1 | 1/2009 | Rothberg |
| 2009/0127589 A1 | 5/2009 | Rothberg |
| 2009/0275486 A1 | 11/2009 | Kurn |
| 2010/0137143 A1 | 6/2010 | Rothberg |
| 2010/0188073 A1 | 7/2010 | Rothberg |
| 2010/0197507 A1 | 8/2010 | Rothberg |
| 2010/0204050 A1* | 8/2010 | Donner ............... C12Q 1/6806 506/3 |
| 2010/0301398 A1 | 12/2010 | Rothberg |
| 2011/0124052 A1* | 5/2011 | Zheng ................. C12Q 1/6844 435/91.2 |
| 2011/0224105 A1 | 9/2011 | Kurn |
| 2011/0275486 A1 | 11/2011 | Hsu |
| 2012/0301926 A1 | 11/2012 | Chen |

FOREIGN PATENT DOCUMENTS

| | | | |
|---|---|---|---|
| WO | WO 2000/018957 | 4/2000 | |
| WO | WO 2005/010145 | 2/2005 | |
| WO | WO 2006/084132 | 8/2006 | |
| WO | WO 2007/120627 | 10/2007 | |
| WO | WO-2013085918 A1 * | 6/2013 | ............ C12N 15/10 |
| WO | WO 2014/018093 | 1/2014 | |

OTHER PUBLICATIONS

Adessi et al., Solid phase DNA amplification: characteristics of primer attachment and amplification mechanisms, Nucleic Acid Res. 28, E87 (2000).
Bennett, et al., Library construction for ancient genomics: single strand or double strand?, Biotechniques 56(6):289-300 (2014).
Bourgon, et al., High-throughput detection of clinically relevant mutations in archived tumor samples by multiplexed PCR and next-generation sequencing, Clin Cancer Res 20(8):2080-2091 (2014).
Brenner et al., Gene expression analysis by massively parallel signature sequencing (MPSS) on microbead arrays, Nat. Biotechnol. 18:630-634 (2000).
DeAngelis M.M. et al. (1995) Solid-phase reversible immobilization for the isolation of PCR products N.A. Res. 25:4742-3.
Do Hongdo, et al., Reducing sequence artifacts in amplicon-based massively parallel sequencing of formalin-fixed paraffin-embedded DNA by enzymatic depletion of uracil-containing templates, Clinical Chem 59(9):1376-1383 (2013).

(Continued)

*Primary Examiner* — Sahana S Kaup
(74) *Attorney, Agent, or Firm* — Knobbe, Martens, Olson & Bear LLP

(57) ABSTRACT

Embodiments provided herein relate to methods and compositions for preparing nucleic acid libraries. Some embodiments include preparing libraries from nucleic acids obtained from degraded samples, such as ancient samples and fixed samples.

19 Claims, 9 Drawing Sheets

(56) References Cited

OTHER PUBLICATIONS

Dressman et al., Transforming single DNA molecules into fluorescent magnetic particles for detection and enumeration of genetic variations, Proc. Natl. Acad. Sci. USA 100:8817-8822 (2003).

Gu, et al., Genome-scale DNA methylation mapping of clinical samples at single-nucleotide resolution, Nature Methods 7(2):133-136 (2010).

Kernesa, et al., Accurate single nucleotide variant detection in viral populations by combining probabilistic clustering with a statistical test of strand bias, BMC Genomics 14(1):501 (2013).

Lizardi et al., Mutation detection and single-molecule counting using isothermal rolling-circle amplification, Nat. Genet. 19:225-232 (1998).

MacLean et al., Application of 'next-generation' sequencing technologies to microbial genetics Nature Rev. Microbiol, 7-287-296 (2009).

Margulies et al., 2005 Genome sequencing in microfabricated high-density picolitre reactors Nature 437, 376-380.

Mitra et al., 2003, Fluorescent in situ sequencing on polymerase colonies Analytical Biochemistry 320, 55-65.

Shendure et al., Accurate Multiplex Polony Sequencing of an evolved Bacterial Genome, Science 309, 1728-1732 (2005).

Voelkerding et al., Next-generation sequencing: from basic research to diagnostics Clinical Chem., 55: 641-658, (2009).

Wood, et al., Using next-generation sequencing for high resolution multiplex analysis of copy number variation from nanogram quantities of DNA from formalin-fixed paraffin-embedded specimens, Nucleic Acids Res 38(14): 1-11 (2010).

Yamtich J, et al (2010). DNA polymerase family X: function, structure, and cellular roles Biochim. Biophys. Acta 1804: 1136-50.

\* cited by examiner

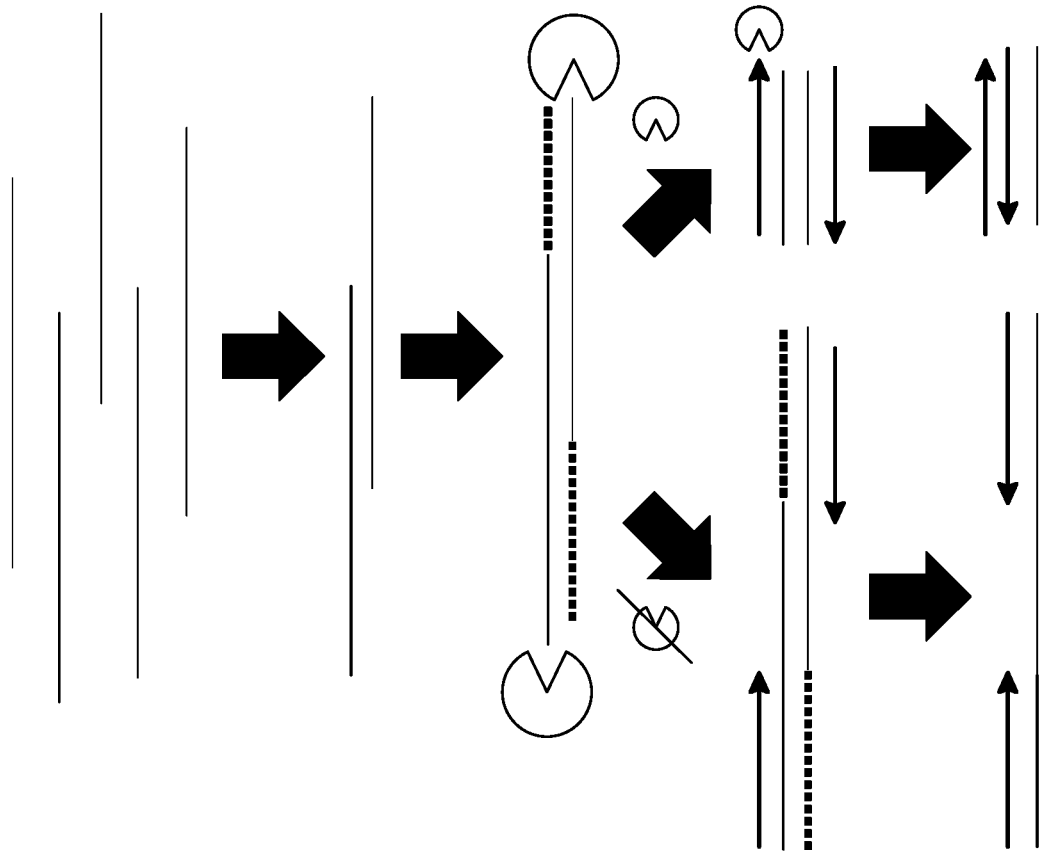

FIG. 8

- 6% of the genome is L1P Long interspersed elements (LINEs)
- They are >97% identical
- In a fragmented pool of ssDNA similar L1P elements from different genomic locations may hybridise
- Without RecJ, during end repair a chimeric dsDNA fragment is formed (it's what happens with our competitors)
- With RecJ, ssDNA is degraded producing short dsDNA fragments
- Paired end sequencing
- During alignment:
  - with no RecJ chimeric fragments are aligned within a normal fragment length of each other
  - with RecJ hybridised fragments are aligned as overlapping reads

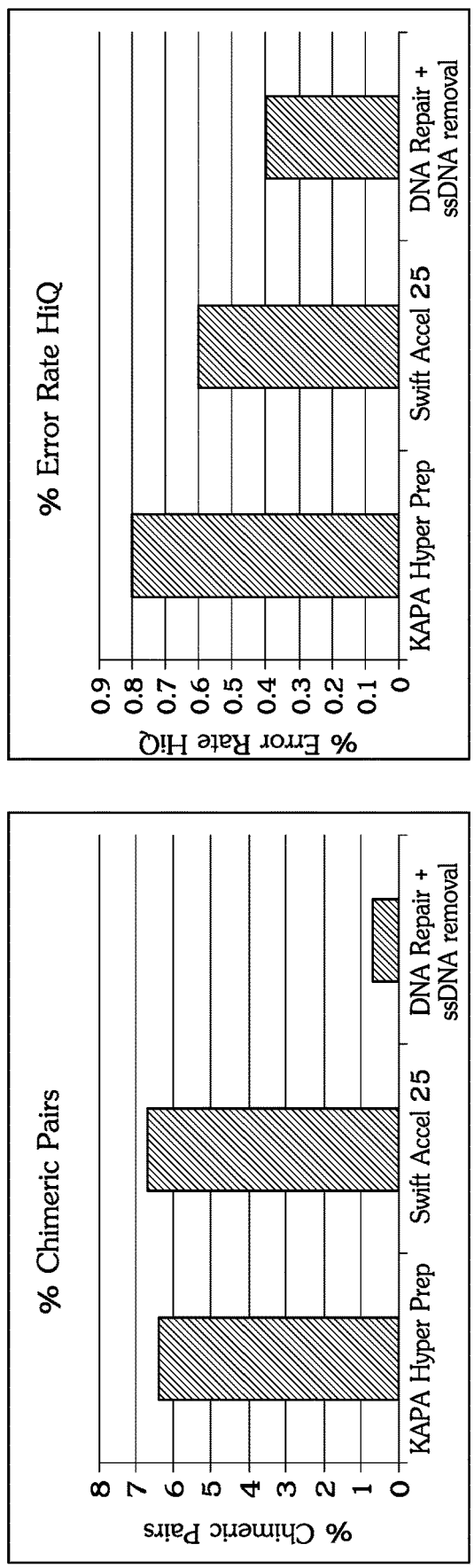
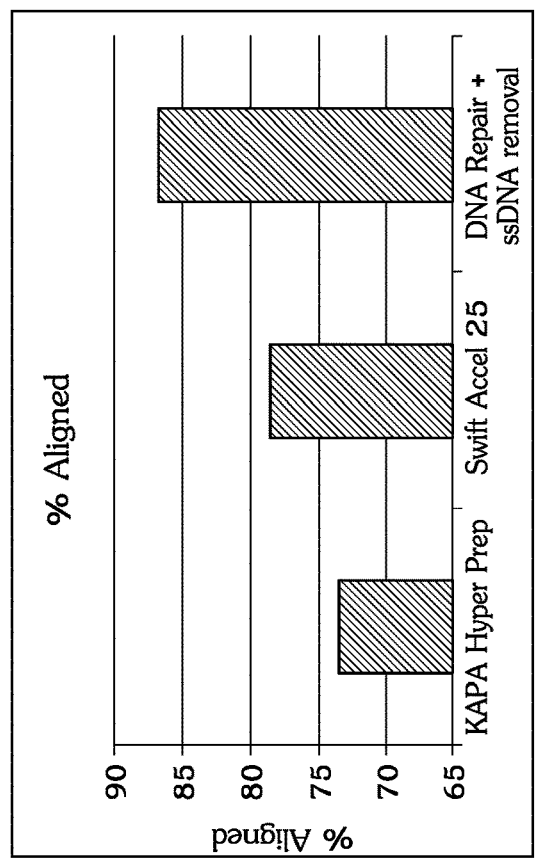
FIG. 9

METHODS AND COMPOSITIONS FOR PREPARING NUCLEIC ACID LIBRARIES

RELATED APPLICATIONS

This application is a continuation of U.S. application Ser. No. 17/068,062 filed Oct. 12, 2020 which is a continuation of U.S. application Ser. No. 16/703,527 filed Dec. 4, 2019 now U.S. Pat. No. 10,988,797 issued Apr. 27, 2021 which is a continuation of U.S. application Ser. No. 16/372,793 filed Apr. 2, 2019 now U.S. Pat. No. 10,683,532 issued Jun. 16, 2020 which is a continuation of U.S. application Ser. No. 15/029,103 filed Apr. 13, 2016 now U.S. Pat. No. 10,294,511 issued May 21, 2019 which is the U.S. National Phase of PCT App. No. PCT/US2014/060942 filed Oct. 16, 2014 and published in English as WO 2015/057985 on Apr. 23, 2015 which claims the benefit of U.S. Prov. App. No. 61/914,204 filed Dec. 10, 2013 and U.S. Prov. App. No. 61/892,220 filed Oct. 17, 2013, the contents of each is incorporated by reference in its entirety.

FIELD OF THE DISCLOSURE

Embodiments provided herein relate to methods and compositions for preparing nucleic acid libraries. Some embodiments include preparing libraries from nucleic acids obtained from low quality nucleic acid samples, such as ancient samples and fixed samples.

BACKGROUND OF THE DISCLOSURE

Whole genome sequencing, genotyping, targeted resequencing, and gene expression analyses of tissue samples can be of significant importance for the identification of disease biomarkers, for the accurate diagnosis and prognosis of disease, and for the selection of a patient's treatment. For example, nucleic acid sequence analysis of tumor tissue excised from a patient can be used to determine the presence or absence of particular genetic biomarkers, e.g., somatic variants, structural rearrangements, point mutations, deletions, and insertions, and/or the presence or absence of particular genes. In addition, analysis of ancient nucleic acids can yield a wealth of information including the evolution of genes and organisms, and the migration and ancestry of populations and individuals.

Fixed tissue samples, such as formalin-fixed and paraffin-embedded (FFPE) pathological samples, are often prepared from patients for histological analysis and archival storage. Nucleic acids in such FFPE samples are often of low quality with significant fragmentation, an increased proportion of single stranded DNA, and a variety of chemically induced DNA lesions including strand breakage, abasic sites and chemically modified bases. Often the amount of DNA that can be extracted from FFPE samples and then analyzed is small. Similarly, ancient nucleic acid samples are often of low quality with factors such as time, temperature, and the presence of water degrading the nucleic acids. Ancient nucleic acids may contain a large number of mutations that increase with time, such as substitutions from the deamination of residues.

The quality and small amounts of DNA that may be prepared from low quality nucleic acid samples make such samples difficult to use in preparing sequencing libraries of sufficient yield, complexity and genomic coverage. Thus, methods and compositions are desirable for the enrichment of nucleic acids obtained from low quality nucleic acid samples that are suitable for nucleic acid sequence analysis.

SUMMARY OF THE DISCLOSURE

Some of the methods and compositions provided herein include a method for preparing a nucleic acid library from a low quality nucleic acid sample comprising: (a) providing a plurality of nucleic acids obtained from the low quality nucleic acid sample; and (b) selectively shearing the plurality of nucleic acids comprising: (i) obtaining a first fraction comprising longer nucleic acids of the plurality of nucleic acids, and a second fraction comprising shorter nucleic acids of the plurality of nucleic acids, (ii) shearing the nucleic acids of the first fraction, and (iii) combining the first fraction and the second fraction, thereby preparing the nucleic acid library.

In some embodiments, step (i) comprises contacting the plurality of nucleic acids with a matrix under conditions wherein nucleic acids greater than about 100 bp selectively bind to the matrix. In some embodiments, step (i) comprises contacting the plurality of nucleic acids with a matrix under conditions wherein nucleic acids greater than about 550 bp selectively bind to the matrix.

In some embodiments, the matrix comprises a solid phase reversible immobilisation (SPRI) bead solution. In some embodiments, the SPRI bead solution is selected from the group consisting of AMPURE XP, SPRISELECT, AXYPREP MAG FRAGMENTSELECT, and MAGJET Magnetic Beads.

In some embodiments, shearing the nucleic acids comprises a step selected from the group consisting of sonicating, acoustic shearing, nebulizing, needle shearing, and enzymatic fragmenting.

In some embodiments, the second fraction comprises nucleic acids less than about 550 bp. In some embodiments, the second fraction comprises nucleic acids less than about 100 bp. In some embodiments, the second fraction essentially consists of nucleic acids less than about 550 bp. In some embodiments, the second fraction essentially consists of nucleic acids less than about 100 bp.

Some embodiments also include repeating (i) and (ii).

Some embodiments also include step (c) removing single-stranded nucleic acids from the combined fractions. Some embodiments also include removing the single-stranded portion of a nucleic acid comprising a single-stranded portion and a double-stranded portion. In some embodiments, step (c) comprises contacting the nucleic acids with a single-strand exonuclease. In some embodiments, the single-strand exonuclease is a 5'-3' exonuclease. In some embodiments, the single-strand exonuclease is selected from the group consisting of RecJ, Exonuclease I, Exonuclease T, Exonuclease VII, Exonuclease VIII, and Mung bean Exonuclease.

Some embodiments also include step (d) repairing the nucleic acids of the combined fractions. In some embodiments, step (d) comprises contacting the nucleic acids with an enzyme selected from the group consisting of Uracil N-Glycosylase (UNG), Uracil DNA Glycosylase (UDG), Endonuclease IV, Endonuclease VIII, formamidopyrimidine-DNA glycosylase (FPG), DNA-(apurinic or apyrimidinic site) lyase, and Pol β.

Some embodiments also include an end repair step. The end repair step can comprise, for example, treating double stranded DNA with a DNA polymerase to generate blunt-ended DNA fragments. In some embodiments, the DNA polymerase can be a polymerase having 5'-3' polymerase activity and 3'-5' exonuclease activity. In some embodiments, the end repair step can comprise treating double stranded DNA fragments with a polynucleotide kinase to generate fragments with 5' phosphates to allow ligation of adapters. In some embodiments, the method also comprises ligating adapters to the nucleic acids of the prepared library.

In some embodiments, the plurality of nucleic acids is selected from the group consisting of DNA, genomic DNA, cDNA, RNA, and circulating tumor DNA (ctDNA).

In some embodiments, the low quality nucleic acid sample comprises a fixed sample. In some embodiments, the fixed sample is fixed with a compound selected from the group consisting of formalin, glutaraldehyde, alcohol, osmic acid, and paraformaldehyde. In some embodiments, the sample is paraffin-embedded. In some embodiments, the sample is a formalin fixed paraffin-embedded sample selected from the group consisting of a fine needle aspirate (FNA), a core biopsy, and a needle biopsy.

In some embodiments, the low quality nucleic acid sample comprises ancient nucleic acids.

Some of the methods and compositions provided herein include a method for preparing a nucleic acid library from a low quality nucleic acid sample comprising: (a) providing a plurality of nucleic acids obtained from the low quality nucleic acid sample; (b) selectively shearing the plurality of nucleic acids comprising: (i) obtaining a first fraction comprising longer nucleic acids of the plurality of nucleic acids, and a second fraction comprising shorter nucleic acids of the plurality of nucleic acids, (ii) shearing the nucleic acids of the first fraction, and (iii) combining the first fraction and the second fraction; and (c) repairing the nucleic acids of the combined fractions, thereby preparing the nucleic acid library.

In some embodiments, step (c) comprises contacting the nucleic acids with an enzyme selected from the group consisting of Uracil N-Glycosylase (UNG), Uracil DNA Glycosylase (UDG), Endonuclease IV, Endonuclease VIII, formamidopyrimidine-DNA glycosylase (FPG), DNA-(apurinic or apyrimidinic site) lyase, and Pol β.

In some embodiments, step (i) comprises contacting the plurality of nucleic acids with a matrix under conditions wherein nucleic acids greater than about 100 bp selectively bind to the matrix. In some embodiments, step (i) comprises contacting the plurality of nucleic acids with a matrix under conditions wherein nucleic acids greater than about 550 bp selectively bind to the matrix.

In some embodiments, the matrix comprises a solid phase reversible immobilisation (SPRI) bead solution. In some embodiments, the SPRI bead solution is selected from the group consisting of AMPURE XP, SPRISELECT, AXY-PREP MAG FRAGMENTSELECT, and MAGJET Magnetic Beads.

In some embodiments, shearing the nucleic acids comprises a step selected from the group consisting of sonicating, acoustic shearing, nebulizing, needle shearing, and enzymatic fragmenting.

In some embodiments, the second fraction comprises nucleic acids less than about 550 bp. In some embodiments, the second fraction comprises nucleic acids less than about 100 bp. In some embodiments, the second fraction essentially consists of nucleic acids less than about 550 bp. In some embodiments, the second fraction essentially consists of nucleic acids less than about 100 bp.

Some embodiments also include repeating (i) and (ii).

Some embodiments also include step (d) removing single-stranded nucleic acids from the combined fractions. Some embodiments also include removing the single-stranded portion of a nucleic acid comprising a single-stranded portion and a double-stranded portion. In some embodiments, step (d) comprises contacting the nucleic acids with a single-strand exonuclease. In some embodiments, the single-strand exonuclease is a 5'-3' exonuclease. In some embodiments, the single-strand exonuclease is selected from the group consisting of RecJ, Exonuclease I, Exonuclease T, Exonuclease VII, Exonuclease VIII, and Mung bean Exonuclease. In some embodiments, an optional step of stopping the exonuclease reaction is included. For example, EDTA can be added to the reaction mixture to inactivate the exonuclease.

Some embodiments also include ligating adapters to the nucleic acids of the prepared library.

In some embodiments, the plurality of nucleic acids is selected from the group consisting of DNA, genomic DNA, cDNA, RNA, and circulating tumor DNA (ctDNA).

In some embodiments, the low quality nucleic acid sample comprises a fixed sample. In some embodiments, the fixed sample is fixed with a compound selected from the group consisting of formalin, glutaraldehyde, alcohol, osmic acid, and paraformaldehyde. In some embodiments, the sample is paraffin-embedded. In some embodiments, the sample is a formalin fixed paraffin-embedded sample selected from the group consisting of a fine needle aspirate (FNA), a core biopsy, and a needle biopsy.

In some embodiments, the low quality nucleic acid sample comprises ancient nucleic acids.

Some of the methods and compositions provided herein include a method for preparing a nucleic acid library from a low quality nucleic acid sample comprising: (a) providing a plurality of nucleic acids obtained from the low quality nucleic acid sample; (b) removing single-stranded nucleic acids from the plurality of nucleic acids; and (c) repairing the nucleic acids of the plurality of nucleic acids, thereby preparing a nucleic acid library.

In some embodiments, step (b) is performed before step (c).

In some embodiments, step (c) is performed before step (b).

In some embodiments, step (b) comprises removing the single-stranded portion of a nucleic acid comprising a single-stranded portion and a double-stranded portion. In some embodiments, step (b) comprises contacting the nucleic acids with a single-strand exonuclease. In some embodiments, the single-strand exonuclease is a 5'-3' exonuclease. In some embodiments, the single-strand exonuclease is selected from the group consisting of RecJ, Exonuclease I, Exonuclease T, Exonuclease VII, Exonuclease VIII, and Mung bean Exonuclease. In some embodiments, an optional step of stopping the exonuclease reaction is included. For example, EDTA can be added to the reaction mixture to inactivate the exonuclease.

In some embodiments, step (c) comprises contacting the nucleic acids with an enzyme selected from the group consisting of Uracil N-Glycosylase (UNG), Uracil DNA Glycosylase (UDG), Endonuclease IV, Endonuclease VIII, formamidopyrimidine-DNA glycosylase (FPG), DNA-(apurinic or apyrimidinic site) lyase, and Pol β.

In some embodiments, step (a) further comprises shearing the plurality of nucleic acids. In some embodiments, the shearing comprises selectively shearing the plurality of nucleic acids comprising: (i) obtaining a first fraction comprising longer nucleic acids of the plurality of nucleic acids, and a second fraction comprising shorter nucleic acids of the plurality of nucleic acids, (ii) shearing the nucleic acids of the first fraction, and (iii) combining the first fraction and the second fraction, thereby preparing the nucleic acid library.

In some embodiments, step (i) comprises contacting the plurality of nucleic acids with a matrix under conditions wherein nucleic acids greater than about 100 bp selectively bind to the matrix. In some embodiments, step (i) comprises contacting the plurality of nucleic acids with a matrix under conditions wherein nucleic acids greater than about 550 bp selectively bind to the matrix.

In some embodiments, the matrix comprises a solid phase reversible immobilisation (SPRI) bead solution. In some embodiments, the SPRI bead solution is selected from the group consisting of AMPURE XP, SPRISELECT, AXY-PREP MAG FRAGMENTSELECT, and MAGJET Magnetic Beads.

In some embodiments, shearing the plurality of nucleic acids comprises a step selected from the group consisting of sonicating, acoustic shearing, nebulizing, needle shearing, and enzymatic fragmenting.

In some embodiments, the second fraction comprises nucleic acids less than about 550 bp. In some embodiments, the second fraction comprises nucleic acids less than about 100 bp. In some embodiments, the second fraction essentially consists of nucleic acids less than about 550 bp. In some embodiments, the second fraction essentially consists of nucleic acids less than about 100 bp.

Some methods also include repeating (i) and (ii).

Some methods also include ligating adapters to the nucleic acids of the prepared library.

In some embodiments, the plurality of nucleic acids is selected from the group consisting of DNA, genomic DNA, cDNA, RNA, and circulating tumor DNA (ctDNA).

In some embodiments, the low quality nucleic acid sample comprises a fixed sample. In some embodiments, the fixed sample is fixed with a compound selected from the group consisting of formalin, glutaraldehyde, alcohol, osmic acid, and paraformaldehyde. In some embodiments, the sample is paraffin-embedded. In some embodiments, the sample is a formalin fixed paraffin-embedded sample selected from the group consisting of a fine needle aspirate (FNA), a core biopsy, and a needle biopsy.

Also provided herein is a method for preparing a nucleic acid library from a low quality nucleic acid sample comprising single stranded DNA, the method comprising: (a) providing a plurality of nucleic acids obtained from the low quality nucleic acid sample, the nucleic acids comprising single stranded DNA; (b) hybridizing random primers to the single stranded DNA and extending the primers to form double stranded DNA; and (c) treating the double stranded DNA to remove single strand overhangs to form blunt ended DNA, thereby preparing a nucleic acid library. In some embodiments, step (c) comprises treating double stranded DNA with a DNA polymerase to generate blunt-ended DNA fragments. In some embodiments, step (c) comprises treating double stranded DNA fragments with a polynucleotide kinase to generate fragments with 5' phosphates to allow ligation of adapters. In some embodiments, the method can further comprise a DNA repair step comprising contacting the nucleic acids with an enzyme selected from the group consisting of Uracil N-Glycosylase (UNG), Uracil DNA Glycosylase (UDG), Endonuclease IV, Endonuclease VIII, formamidopyrimidine-DNA glycosylase (FPG), DNA-(apurinic or apyrimidinic site) lyase, and Pol β. In some embodiments, the DNA repair step is performed prior to step (b). In some embodiments, the DNA repair step is performed after step (b). In some embodiments, the DNA repair step is performed prior to step (c). In some embodiments, the DNA repair step is performed after step (c).

Some of the methods and compositions provided herein include a nucleic acid library prepared by the method of any one of the foregoing methods.

Some of the methods and compositions provided herein include a method for sequencing a nucleic acid comprising: obtaining a nucleic acid library prepared according to any one of the foregoing methods; and sequencing at least a portion of the nucleic acid library, thereby sequencing the nucleic acid.

BRIEF DESCRIPTION OF THE DRAWINGS

FIG. 8 depicts a mechanism by which single-stranded species can introduce chimeric pairs resulting in misalignments during paired end sequencing.

FIG. 9 shows a series of graphs setting forth the results of a comparative analysis of various workflows and demonstrating that performing DNA repair and ssDNA removal yields significant improvements in the following metrics: % chimeric pairs, % error rate, and % aligned.

DETAILED DESCRIPTION

Embodiments provided herein relate to methods and compositions of preparing nucleic acid libraries. Some embodiments include preparing libraries from nucleic acids obtained from low quality nucleic acid samples, such as fixed samples and ancient samples.

Figure 1:
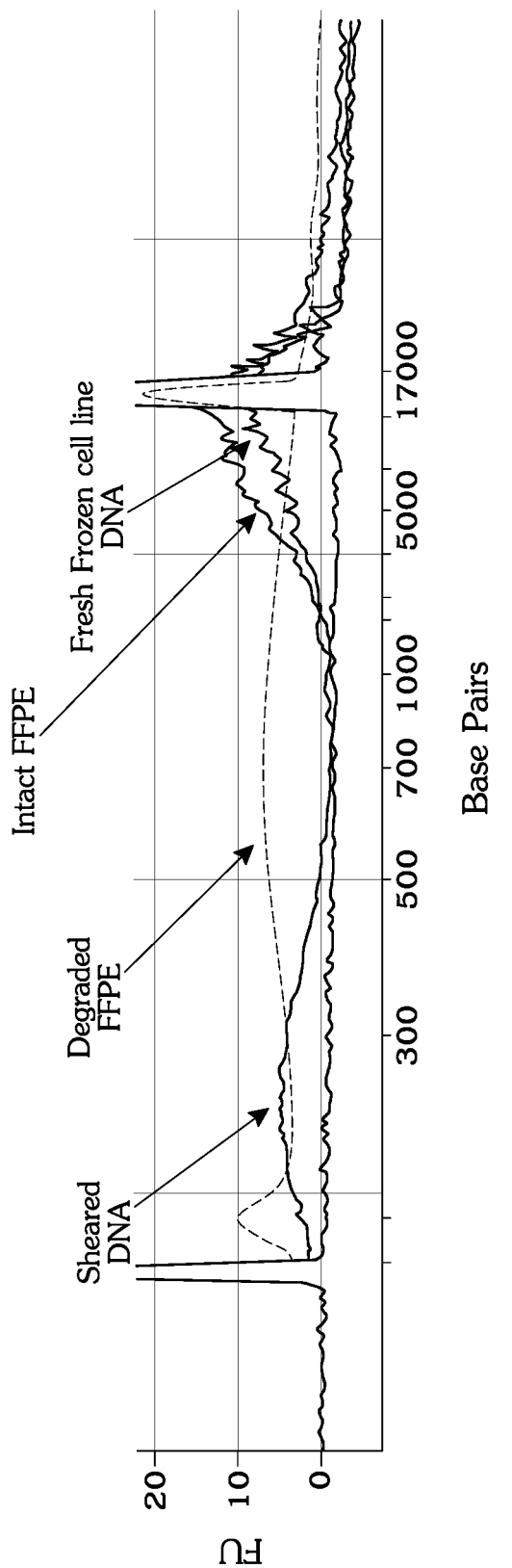
FIG. 1 is a graph depicting the nucleic acid fragment size distribution for acoustically sheared DNA, unfragmented DNA extracted from a freshly frozen cell line, highly degraded FFPE DNA, and relatively intact DNA samples extracted from different FFPE tissue samples.

Nucleic acids in fixed samples can become heavily fragmented and chemically modified due to the fixation and embedding methods used. Such fragmentation and modification can increase over time. Therefore, nucleic acids isolated from fixed samples are often of a lower molecular weight than those obtained from fresh or frozen samples. Fixed nucleic acid samples, such as FFPE DNA are often degraded and a poor substrate for preparing a nucleic acid library for sequence analysis. FIG. 1 shows an example of nucleic acid fragment size distribution for acoustically sheared DNA, untreated genomic DNA extracted from a freshly frozen cell line, and untreated DNA from two different FFPE tissue samples in which the respective samples are highly fragmented or relatively intact. The fragmentation of some FFPE DNA results in the loss of a substantial proportion of the material when preparing libraries using known methods. This loss results in libraries with low diversity or complexity (defined as the number of unique DNA fragments in the sample), that are unsuitable for use in applications such as the deep sequencing of complex genomes.

Figure 2:
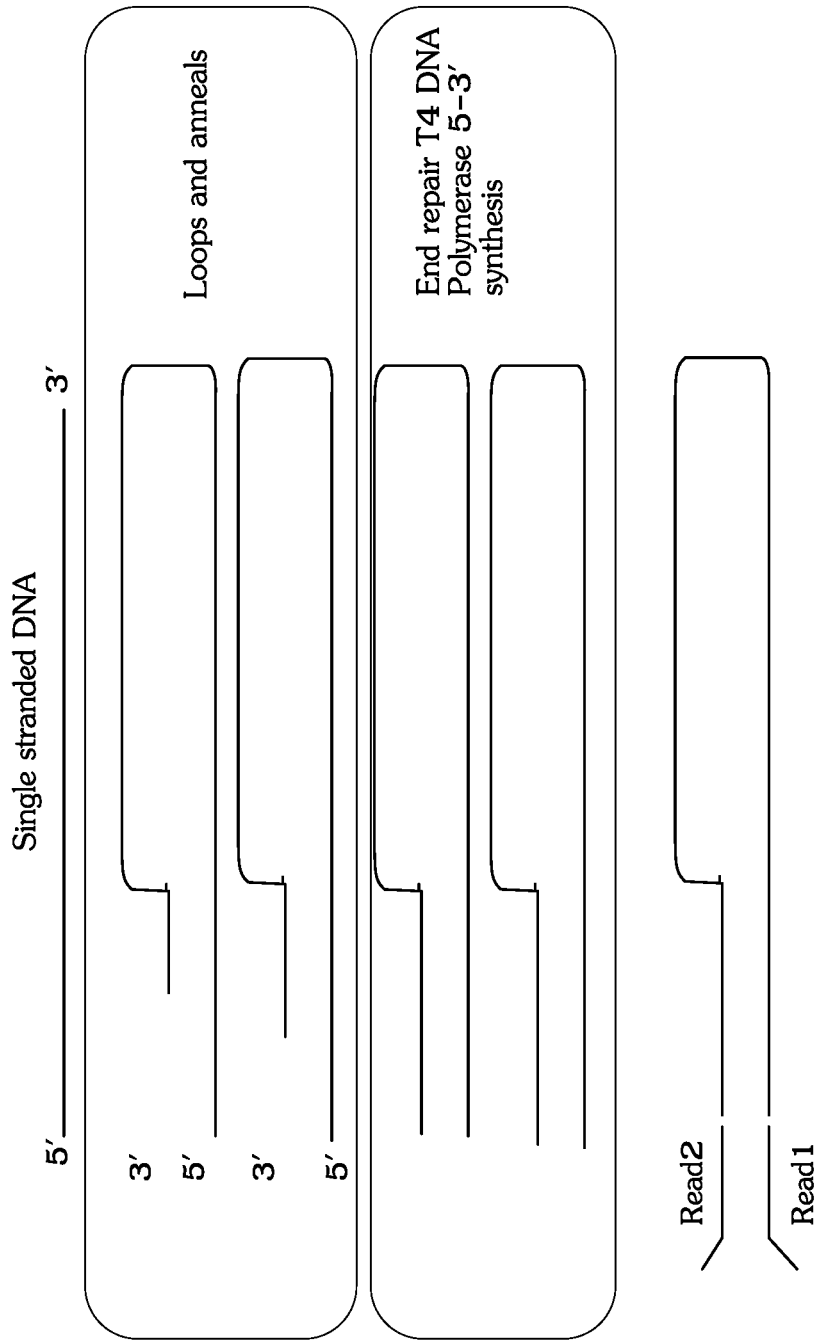
FIG. 2 depicts a mechanism by which single-stranded species can introduce artifacts in a nucleic acid library. During library construction single-stranded DNAs may each form a loop which may be end-repaired with T4 DNA polymerase during library construction, adaptors exemplified as Read1 and Read2 may be ligated to the ends of each looped structure. Subsequent reads of libraries with such looped structures have increased mismatch rates and lower percentage alignment rates.

In addition, FFPE DNA may include significant levels of single-stranded species that arise both from the harsh extraction methods employed and the fact that the DNA is fragmented into short duplexes that may be thermally unstable. Such single-strand species can also be problematic in nucleic acid library preparation methods. For example, in methods that include end-repair and double stranded ligation, adaptors may be ligated at double-stranded ends of partially self-complementary single-stranded DNA molecules. FIG. 2 shows an example in which two single-stranded DNAs each form a loop which may be end-repaired, and adaptors designated Read 1 and Read 2 ligated to the loop. Such looped structures may lead to artifact reads with increased mismatch rates and lower percentage aligning. FFPE DNA may also contain higher levels of modified bases, for example, C to T and G to A substitutions that may lead to false variant calls and reduced levels of alignment between a series of sequenced nucleic acids, and also render the DNA non-amplifiable by certain DNA polymerases.

Similar to fixed nucleic acid samples, ancient nucleic samples can be of low quality. Ancient samples can include populations of nucleic acids with a significant fraction of shorter nucleic acids, and a significant fraction of single-stranded species. In addition, ancient nucleic acids may contain a large number of mutations that increase with time, such as substitutions from the deamination of residues.

Figure 3:
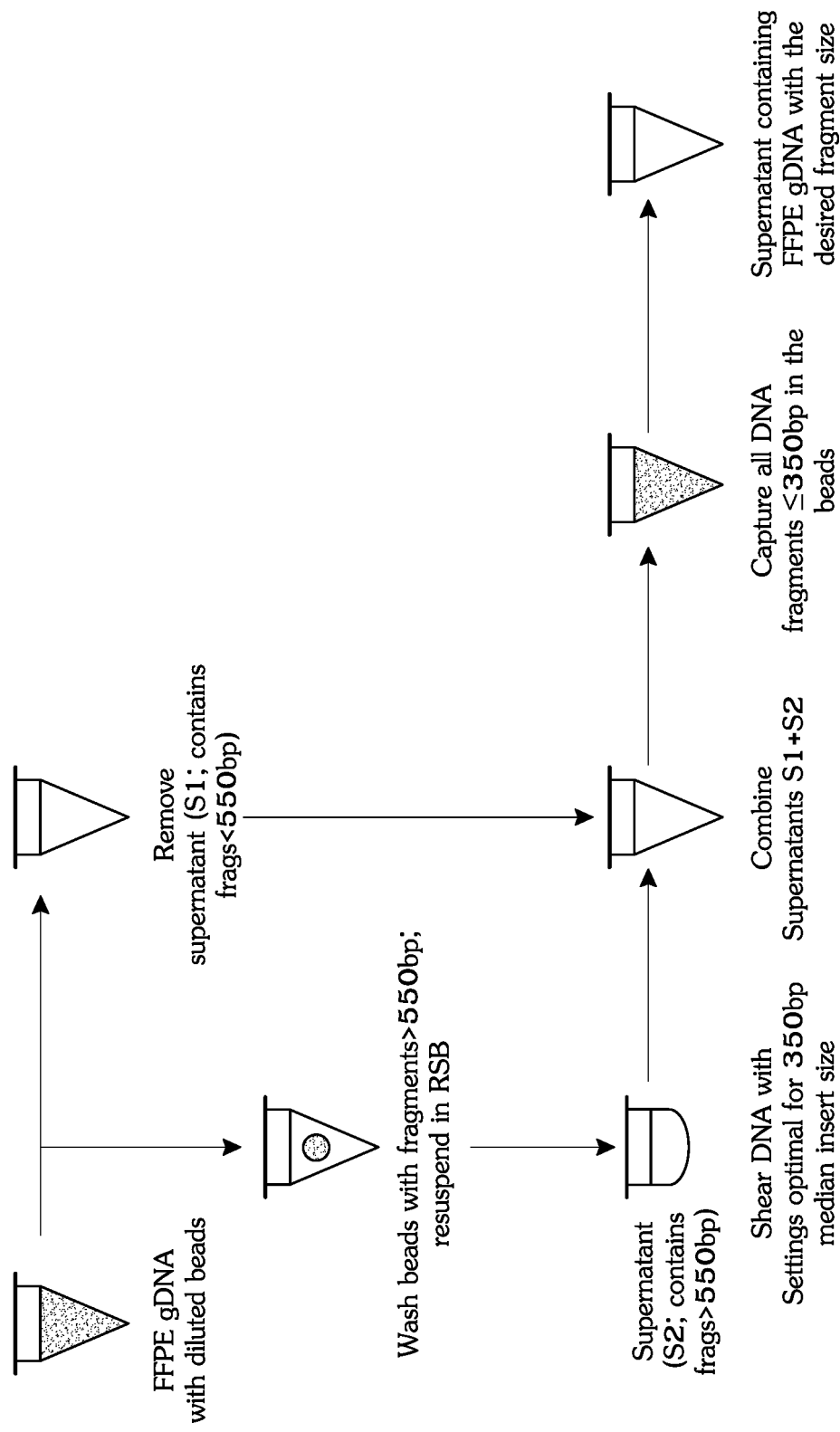
FIG. 3 depicts an example workflow for selectively shearing nucleic acids obtained from a FFPE biological sample in which smaller DNA fragments (<550 bp) are initially removed, larger DNA fragments (>550 bp) are sheared in order to obtain a population with a desired size.
Figure 4:
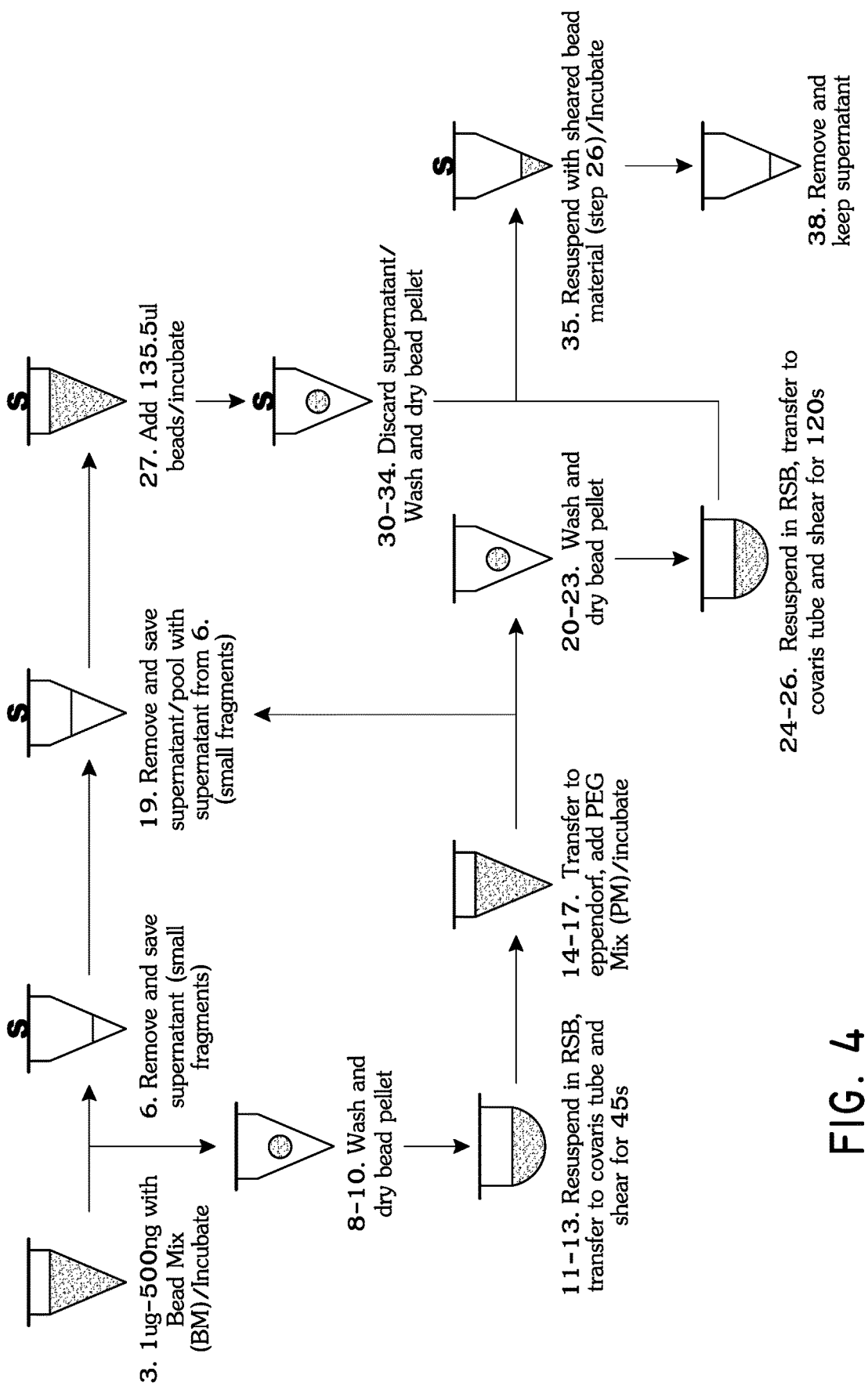
FIG. 4 depicts an example of an extended work flow for selectively shearing nucleic acids obtained from a FFPE biological sample.
Figure 5:
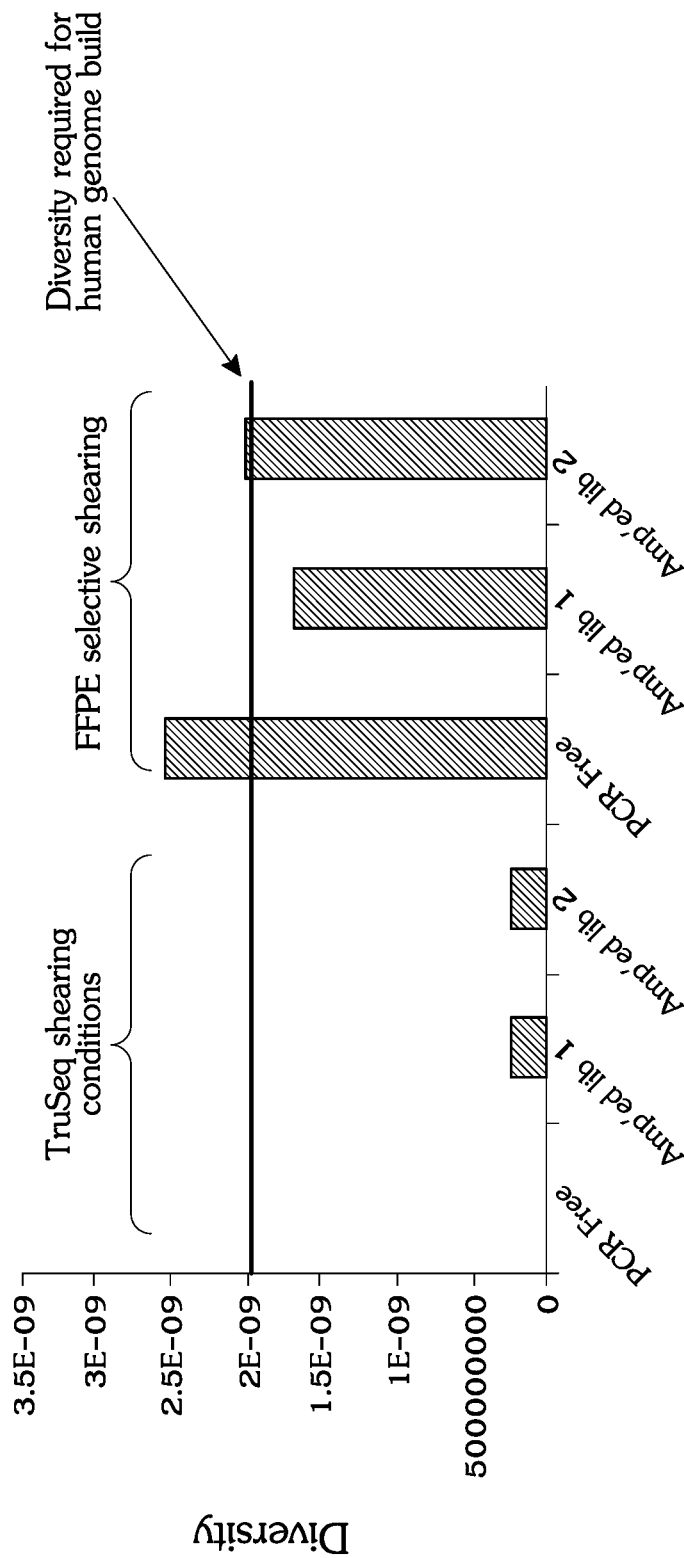
FIG. 5 is a graph depicting estimated levels of nucleic acid diversity in various samples of nucleic acids prepared under either TRUSEQ shearing conditions, or selective shearing conditions. Nucleic acid diversity can be estimated from the number of unique DNA fragments calculated to be present within the sample from sequence information.

Some embodiments of the methods and compositions provided herein enrich for nucleic acids useful for nucleic acid library preparation. Some such embodiments include selectively shearing nucleic acids obtained from a low quality nucleic acid samples, such as a fixed sample, such as a FFPE sample. Selective shearing includes isolating shorter nucleic acid from a sample prior to the deliberate shearing of the remaining longer nucleic acids in the sample. In such methods, the shorter nucleic acids are not lost by being sheared to a size that is not useful for library preparation. Both the shorter nucleic acids and sheared nucleic acids can then be re-combined to produce a sample containing a substantially higher yield of fragments of the desired size. FIG. 3 depicts an example workflow for selectively shearing nucleic acids obtained from a FFPE biological sample in which smaller DNA fragments (<550 bp) are initially removed, larger DNA fragments (>550 bp) are sheared in order to obtain a population with a desired size. Advantageously, selective shearing increases the diversity of nucleic acid species in a prepared nucleic acid library. Shorter nucleic acids are captured prior to shearing longer nucleic acid fragments in a nucleic acid sample. The captured shorter fragments are then re-combined with the sheared nucleic acids. Selective shearing improves library diversity and can enable at least a thirty-fold increase in the number of genome builds from a prepared nucleic acid library. FIG. 4 depicts an example extended workflow of selectively shearing nucleic acids obtained from a FFPE biological sample. FIG. 5 is a graph depicting the number of unique DNA fragments (diversity) in various samples of nucleic acids prepared under either TRUSEQ shearing conditions, or selective shearing conditions. Nucleic acid samples obtained from FFPE samples and further prepared using certain proprietary protocols were subjected to either TRUSEQ shearing conditions, or selective shearing conditions. The nucleic acid populations that were subjected to selective shearing conditions included those with a diversity sufficient for genomic builds from a prepared nucleic acid library. In some embodiments, shearing is performed on a sample which includes both smaller and larger DNA fragments. It is contemplated that shearing of the sample may help reverse cross linking of the DNA fragments in a FFPE sample.

Figure 6:
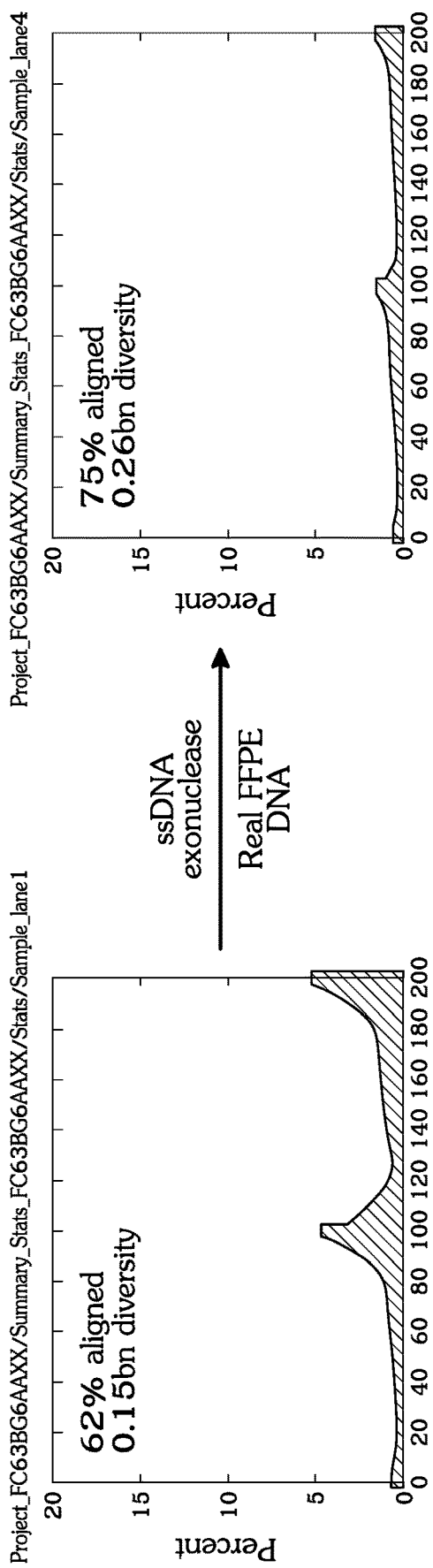
FIG. 6 shows the percent mismatch rates (y-axis; 0%-20%) with increasing sequencing cycle number (x-axis; 0-200 cycles) obtained from sequencing of an FFPE derived DNA library before (left panel) and after (right panel) treatment of the DNA with a single-strand exonuclease.

In addition to selective shearing, some embodiments of the methods and compositions provided herein for enriching nucleic acids useful for nucleic acid library preparation include removing single-strand species of nucleic acids and 5' overhangs from nucleic acids obtained from low quality nucleic acid samples, such as a fixed sample, such as a FFPE sample. For example, removal of single-stranded DNA and 5' overhanging species formed from self-complementary single-stranded DNA using exonuclease treatment can improve the percentage of a population of nucleic acids in a prepared nucleic acid library to be aligned, improve diversity of the prepared library, and reduce read pairings artifacts. FIG. 6 depicts graphs of the level before treatment of FFPE DNA with a single-strand exonuclease (left panel), and after treatment of FFPE DNA with a single-strand exonuclease (right panel).

Figure 7:
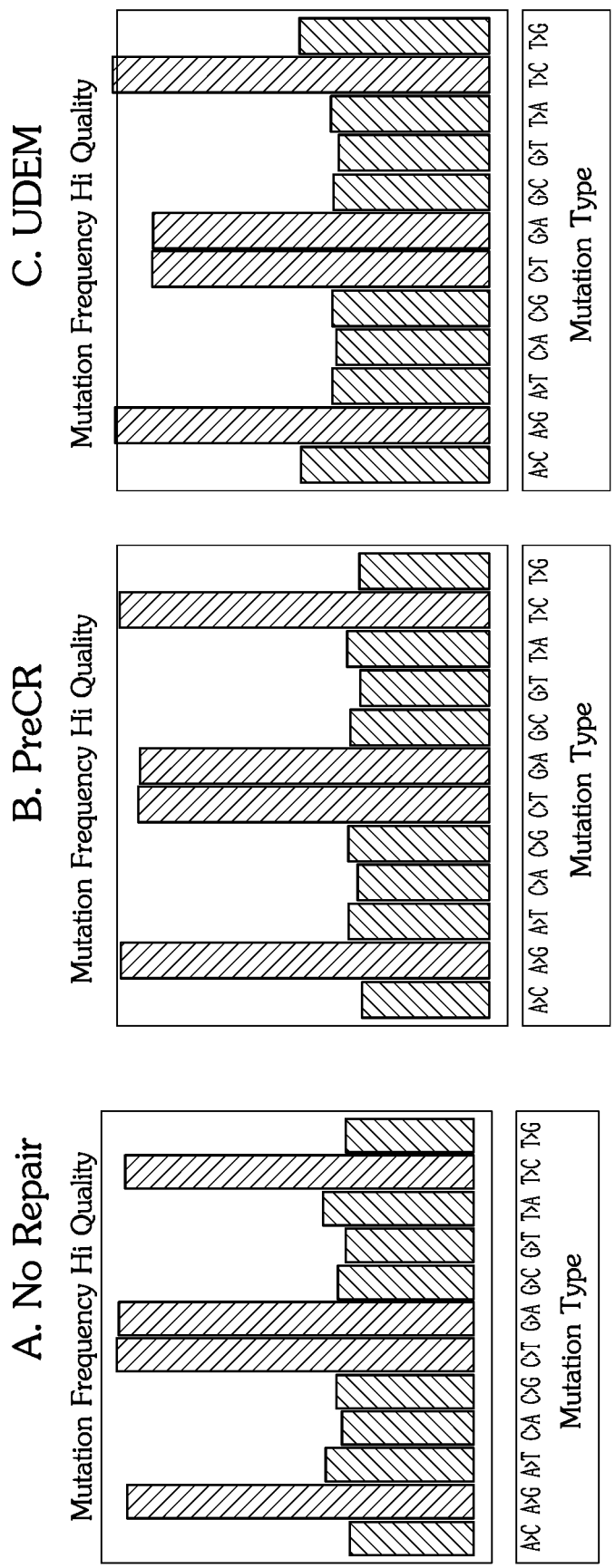
FIG. 7 shows a series of graphs for the number of particular base calls at certain loci in a nucleic acid sequence in which the FFPE template nucleic acid has undergone no repair (panel A), has undergone repair with PreCR repair mix (panel B), or has undergone repair with an Uracil-DNA Excision mix (UDEM) (panel C). In each panel, each column represents the following base changes/mutation types: (leftmost column) A>C; A>G; A>T; C>A; C>G; C>T; G>A; G>C; G>T; T>A; T>C; and T>G (rightmost column). Panel A depicts increased occurrence of incorrectly called bases at certain loci; Panels B and C illustrate decreased occurrence of miscalled bases at certain loci in repaired FFPE DNA sample. PreCR improves the C-T/G-A transitions, UDEM improves it further.

In addition to selective shearing, some embodiments of the methods and compositions provided herein for enriching nucleic acids useful for nucleic acid library preparation include repairing nucleic acids from a low quality nucleic acid samples, such as a fixed sample, such as a FFPE sample. FIG. 7 is a series of graphs demonstrating the levels of particular bases at a locus derived from sequencing a number of nucleic acids with panel A depicting increased occurrence of incorrect base calls in a FFPE DNA sample, panel B and C depicting decreased occurrence of incorrect base calls at the locus in repaired FFPE DNA sample. For example, during processing of FFPE samples DNA can be damaged which results in incorrect base calling upon sequencing. It was determined during experimentation that, in addition to selective shearing, treatment of the sample with an enzyme cocktail, for example PRECR mix (NEB) and/or UDEM (Epicentre) could help correct damaged DNA for more accurate sequencing.

As used herein "nucleic acid" can refer to a polymer comprising ribonucleosides and/or deoxyribonucleosides that are covalently bonded, typically by phosphodiester linkages between subunits, but in some cases by phosphorothioates, methylphosphonates, and the like. Examples of nucleic acids include genomic DNA; circular DNA; low molecular weight DNA, plasmid DNA; circulating DNA, circulating tumor DNA (ctDNA); hnRNA; mRNA; noncoding RNA including rRNA, tRNA, micro RNA, small interfering RNA, small nucleolar RNA, small nuclear RNA and small temporal RNA; fragmented or degraded nucleic acids; PNAs; nucleic acid obtained from subcellular organelles such as mitochondria or chloroplasts; and nucleic acid obtained from microorganisms, parasites, or DNA or RNA viruses that may be present in a biological sample. Synthetic nucleic acid sequences that may or may not include nucleotide analogs that are added or "spiked" into a biological sample are also contemplated.

Samples

Some of the methods and compositions provided herein include preparing libraries from nucleic acids obtained from samples. As used herein "sample" includes a variety of sources and compositions that contain nucleic acids. The sample may be a biological sample but the term also includes other, e.g. artificial samples which comprise nucleic acids such as PCR products or compositions comprising already purified nucleic acids which may be further concentrated and/or further purified. Biological samples include viral particles, cells, tissues, organs, and any portion of an organism. Examples of samples include fixed samples. Fixed samples include samples that have been treated with fixing/cross-linking compounds or agents. Examples of fixing/cross-linking compounds and agents include formalin, glutaraldehyde, alcohol, osmic acid, and paraformaldehyde, and radiation sources, such as electron bean exposure, gamma-radiation, and UV light. Samples may be further treated by embedding the sample in a wax, such as paraffin wax. Samples can include a fine needle aspirate, a core biopsy, and a needle biopsy. Preferred samples include fixed samples, such as FFPE samples, and ancient samples. Ancient samples can include nucleic acids from ancient specimens, including nucleic acids recovered from biological samples that have not been preserved specifically for later DNA analyses. Examples of ancient nucleic acids include nucleic acids recovered from archeological material, historical skeletal material, mummified tissues, archival collections of non-frozen medical specimens, preserved plant remains, ice and permafrost cores, Holocene plankton, marine and lake sediments. Ancient nucleic acids include nucleic acids from a sample that is at least about 1 year old, 5 years old, 10 years old, 20 years old, 50 years old, 100 years old, 500 years old, 1000 years old, and a range between any two of the foregoing ages.

In some embodiments, a sample includes low quality nucleic acids. Low quality nucleic acids include a population of nucleic acids that is a potentially poor substrate for typical methods of nucleic acid library preparation. Examples of poor substrates for nucleic acid library preparation include populations of nucleic acids in which a substantial fraction of the population is single-stranded, is nicked, is mutated, and/or is fragmented. A substantial fraction can include at least about 10%, 20%, 30%, 40%, 50%, 60%, 70%, 80%, 90%, and 95%, and a range between any two of the foregoing parameters. Advantageously, the methods and compositions provided herein include preparing populations of low quality nucleic acids for further preparation of nucleic acid libraries. Further, low quality nucleic acid samples such as FFPE DNA or ancient DNA often have limiting amounts of material, which limits the quantity and quality of sequencing libraries. The methods presented herein are surprisingly effective for generating sequencing libraries from low amounts of input material. For example, in some embodiments, the input material comprises no more than 100 ng, 80 ng, 70 ng, 60 ng, 50 ng, 40 ng, 30 ng, 20 ng, 10 ng, 5 ng, 2 ng, 1 ng or no more than 0.5 ng of input nucleic acid.

In some embodiments, samples include materials obtained from clinical or forensic settings that contain nucleic acids. Preferably, the sample is a biological sample derived from a human, animal, plant, bacteria or fungi. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung, kidney or liver. Furthermore, the skilled artisan will appreciate that lysates, extracts, or processed materials or portions obtained from any of the above exemplary samples are also within the scope of the term "sample". This in particular includes but is not limited to sample lysates, cleared lysates, pre-extracted sample portions which are e.g. enriched for a certain type of target nucleic acid as is e.g. the case during a phenol/chloroform extraction wherein nucleic acids such as RNA are concentrated in the aqueous phase, purified nucleic acids which are supposed to be further purified and/or concentrated and the like.

Method of Preparing Nucleic Acid Libraries

Some of the methods and compositions provided herein include preparing libraries from nucleic acids obtained from samples comprising low quality nucleic acids, such as fixed samples. Some such embodiments include obtaining a nucleic acid sample from a fixed sample. Methods of obtaining nucleic acids from a fixed sample are well known in the art. In some embodiments, a sample, such as a paraffin-embedded sample may undergo deparaffinization. Deparaffinization removes the bulk of paraffin from a paraffin-embedded sample. In some embodiments, a sample is washed with an organic solvent to dissolve the paraffin. Such solvents are able to remove paraffin effectively from a sample without adversely affecting nucleic acid isolation. Suitable solvents can be chosen from solvents such as benzene, toluene, ethylbenzene, xylenes, and mixtures thereof. Nucleic acids can be further recovered using methods well known in the art. The methods and compositions disclosed herein are not limited to the method that nucleic acids are extracted from fixed samples.

In some embodiments of the methods and compositions provided herein, nucleic acids are sheared. Methods to shear nucleic acids are well known in the art. Examples include sonication, nebulization, mechanical shearing such as needle shearing, and limited enzyme digestion. In some embodiments, nucleic acids are sheared to provide a population of nucleic acids with an average length of less than about 5000 bp, 1000 bp, 900 bp, 800 bp, 700 bp, 600 bp, 550 bp, 500 bp, 450 bp, 400 bp, 350 bp, 300 bp, 250 bp, 200 bp, 150 bp, 100 bp, 50 bp, 25 bp, and 10 bp, and a range between any two of the foregoing parameters.

In some embodiments, shearing the nucleic acids comprises selectively shearing the nucleic acids. Advantageously, selective shearing retains shorter nucleic acids that may be discarded in other methods of preparation. Selective shearing may be performed on low quality nucleic acids that include a significant portion of shorter nucleic acids that would typically be discarded in other methods of preparation. Selectively shearing nucleic acids includes fractionating and/or enriching a population of nucleic acids to obtain a portion comprising shorter nucleic acids, and a portion comprising longer nucleic acids. In some embodiments, the portion comprising shorter nucleic acids can include nucleic acids with a length less than about 1000 bp, 900 bp, 800 bp, 700 bp, 600 bp, 550 bp, 500 bp, 450 bp, 400 bp, 350 bp, 300 bp, 250 bp, 200 bp, 150 bp, 100 bp, 50 bp, 25 bp, and 10 bp, and a range between any two of the foregoing parameters. In some embodiments, the portion comprising shorter nucleic acids can include nucleic acids with an average length less than about 1000 bp, 900 bp, 800 bp, 700 bp, 600 bp, 550 bp, 500 bp, 450 bp, 400 bp, 350 bp, 300 bp, 250 bp, 200 bp, 150 bp, 100 bp, 50 bp, 25 bp, and 10 bp and a range between any two of the foregoing parameters. In some embodiments, the portion comprising longer nucleic acids can include nucleic acids with a length greater than about 100 bp, 200 bp, 300 bp, 400 bp, 500 bp, 550 bp, 600 bp, 700 bp, 800 bp, 900 bp, 1000 bp, 1 kb, and 5 kb, and a range between any two of the foregoing parameters. In some embodiments, the portion comprising shorter nucleic acids can include nucleic acids with an average length greater than about 100 bp, 200 bp, 300 bp, 400 bp, 500 bp, 550 bp, 600 bp, 700 bp, 800 bp, 900 bp, 1000 bp, 1 kb, and 5 kb, and a range between any two of the foregoing parameters. Methods to fractionate and/or to enrich for nucleic acids by length of nucleic acids include, but are not limited to, gel electrophoresis, chromatographic techniques, and use of a matrix to selectively bind nucleic acids, such as solid phase reversible immobilisation (SPRI) beads, for example a SPRI bead solution. See e.g., DeAngelis M. M. et al. (1995) N. A. Res. 25:4742-3, expressly incorporated by reference in its entirety. Examples of SPRI beads include AMPURE XP (Beckman), SPRISELECT (Beckman Coulter), AXYPREP MAG FRAGMENTSELECT (Aygen Biosciences), and MAGJET Magnetic Beads (Thermo Scientific).

In some embodiments, the steps of fractionating and/or enriching a population of nucleic acids by length, and shearing a portion of the fractionated/enriched nucleic comprising longer nucleic acids can be repeated two times or more. In some embodiments, portions of nucleic acids comprising shorter nucleic acids and the sheared nucleic acids (e.g., resulting from shearing of longer nucleic acids) are combined to provide a substrate for preparing a nucleic acid library.

In some embodiments of the methods and compositions provided herein, single-stranded nucleic acid species are removed from a population of nucleic acids. In some embodiments, single-strand overhangs or other single-strand portions of nucleic acids comprising a single-strand portion, are removed from a population of nucleic acids. Methods to remove single-strand species and/or single-strand overhangs from a population of nucleic acids include, but are not limited to, use of specific enzymes, such as single-strand exonucleases, RecJ, Exonuclease I, and Exonuclease T, Exonuclease VIII, Exonuclease VII, Mung bean Nuclease; and selective hybridization of single-strand species. In some embodiments, an optional step of stopping the exonuclease reaction is included. For example, EDTA can be added to the reaction mixture to inactivate the exonuclease.

In some embodiments of the methods and compositions provided herein, nucleic acids in a population of nucleic acids for preparing a nucleic acid library are repaired. For example, nicks may be filled-in and repaired; overhangs may be copied to form double-stranded segments of a nucleic acid. Methods to repair nucleic acids are well known in the art, as exemplified by the disclosure of WO 2007/120627, which is incorporated herein by reference in its entirety. In some embodiments, repairing nucleic acids can include excision of modified or damaged bases, removal of abasic sites, fill-in of nicks, ligation of nicks ligation, removal of 3' blocking groups, and reversal of crosslinks such as pyrimidine dimers.

In some embodiments, repairing nucleic acids can include contacting the nucleic acids with a DNA glycosylase. DNA glycosylases are a family of enzymes involved in base excision repair by which damaged bases in DNA are removed and replaced. In some embodiments, the nucleic acid molecules may be treated with a uracil DNA glycosylase resulting in a plurality of abasic residues in place of uracil residues. Persons skilled in the art would appreciate that any suitable DNA glycosylase, including but not limited to uracil DNA glycosylases, may be used to convert the uracil residues into abasic residues. For example, UNG (human Uracil-DNA glycosylase), or its orthologs in organisms other than human, may be used. Other suitable polynucleotide cleavage enzymes suitable for use in the nucleic acid repair methods set forth herein can include, for example, the following types of enzymes derived from but not limited to any particular organism or virus: 1) AP endonucleases, such as *E. coli* endonuclease IV, Tth endonuclease IV, and human AP endonuclease; 2) glycosylases, such as UDG, *E. coli* 3-methyladenine DNA glycosylase (AlkA) and human Aag; 3) glycosylase/lyases, such as *E. coli* endonuclease III, *E. coli* endonuclease VIII, *E. coli* Fpg, human OGG1, and T4 PDG; and 4) lyases. In certain typical embodiments, one or more of the following DNA glycosylases may be utilized, including Uracil N-Glycosylase (UNG), Uracil DNA Glycosylase (UDG) and formamidopyrimidine-DNA glycosylase (FPG). In some embodiments, repairing nucleic acids can include removal of abasic sites. An abasic site, also known as an AP site (apurinic/apyrimidinic site), is a location in DNA that has neither a purine nor a pyrimidine base. Abasic sites may be repaired by contacting a nucleic acid with enzymes including, for example, a polymerase such as a Family X polymerase such as Pol β which is required for short-patch base excision repair, a DNA repair pathway that is essential for repairing alkylated or oxidized bases as well as abasic sites (Yamtich J, et al (2010). Biochim. Biophys. Acta 1804: 1136-50); a Class II AP endonucleases such as DNA-(apurinic or apyrimidinic site) lyase encoded by APEX1 gene; and Endonuclease IV which is a type of deoxyribonuclease.

In some embodiments provided herein, a population of nucleic acids from a fixed sample is sheared, single-stranded species and overhangs are removed from the population of nucleic acids, and nucleic acids are repaired. In some embodiments, the shearing is selective shearing. In some embodiments, a population of nucleic acids from a fixed sample can be processed by performing two or more of selective shearing, single stranded species removal, nucleic acid overhang removal and nucleic acid repair prior to library preparation. Some such embodiments can provide a substrate for further nucleic acid library preparation. Methods of preparing a nucleic acid library are well known in the art. Examples include ligating adaptors to the nucleic acids in a population of nucleic acids. In some embodiments, nucleic acid fragments can be blunt-ended, phosphorylated, coupled to A-tails, and/or coupled to adaptors to yield a nucleic acid library. In some embodiments, the nucleic acid library may be further amplified Examples of library preparation protocols include, but are not limited to, methods for Nextera™ DNA Sample Prep Kit (Epicentre® Biotechnologies, Madison Wis.), GL FLX Titanium Library Preparation Kit (454 Life Sciences, Branford Conn.), and the like. The sample as described herein can be further amplified for sequencing or microarray assays by, for example, multiple stand displacement amplification (MDA) techniques. For sequencing after MDA, an amplified sample library is, for example, prepared by creating a DNA library as described in Mate Pair Library Prep kit, Genomic DNA Sample Prep kits or TruSeq™ Sample Preparation or Exome Enrichment kits (Illumina®, Inc., San Diego Calif.). Another useful method for amplifying nucleic acids is rolling circle amplification (RCA), for example, as described in Lizardi et al., Nat. Genet. 19:225-232 (1998) and US 2007/0099208, each of which is incorporated herein by reference in its entirety. Emulsion PCR methods are also useful, exemplary methods which are described in Dressman et al., Proc. Natl. Acad. Sci. USA 100:8817-8822 (2003), WO 05/010145, or U.S. Patent Publ. Nos. 2005/0130173 or 2005/0064460, each of which is incorporated herein by reference in its entirety. Methods of the present disclosure are not limited by any particular library preparation or amplification method.

In one exemplary embodiment for library preparation from FFPE DNA, the method can comprise the following steps. First, DNA is sheared in a non-selective fashion. The shearing can utilize less aggressive or more aggressive shearing conditions, depending on sample quality and downstream applications. DNA repair is then performed, comprising (i) excision of uracil using a uracil DNA excision mix (UDEM), and (ii) removal of single stranded DNA using an exonuclease such as RecJ. The uracil excision and ssDNA removal can occur in any order. Next, end repair is performed to generate blunt-ended fragments for ligation. The end repair reaction can be performed, for example, using a DNA polymerase, such as, for example, T4 DNA polymerase is utilized. The end repair reaction can also further comprise a polynucleotide kinase, such as, for example, T4 polynucleotide kinase. In some embodiments, the polymerase and kinase reactions are combined, and the reaction mixture contains dNTPs and ATP. Size selection can then be performed. In some embodiments, a beads to DNA ratio of 1.2 to 1 is used, but can be varied depending on sample quality and downstream applications. The method can further comprise an A-tailing step, followed by ligation of adapters having a 3' T overhang. An optional clean up step can be performed to remove adapter dimers and unligated fragments. The ligated DNA fragments can optionally be enriched by PCR to amplify fragments with adapters on both ends. This example is only one of a variety of ways to perform the methods described herein.

Preparation of ssDNA

Also provided herein are methods for preparing a nucleic acid library from a low quality nucleic acid sample comprising single stranded DNA. Single stranded DNA is often present as a result of the methods associated with preservation of FFPE samples and extraction of nucleic acids from FFPE samples. In some embodiments one or more primers are hybridized to the single stranded DNA and the primers are extended using a polymerase to form double stranded DNA. The primers can be, for example, of one or more known sequences. In some embodiments, the primers are random primers. Any number of compositions of random primers and methods of using the same as are known in the art can be used in the methods presented herein, as exemplified by the methods and compositions described in WO 2014/018093, the content of which is hereby incorporated by reference in its entirety. The term "random" as used throughout the present disclosure with respect to primers, oligonucleotides, polynucleotides and the like should be understood to refer to degeneracy at one or more positions of a nucleotide. Thus, in certain embodiments, the term random can refer to purely random distribution at all positions, where each position can be equally likely to be any one of the four standard nucleotides. In certain embodiments, the term random can refer to a random distribution at less than all of the nucleotide positions in the polynucleotide. In some embodiments, the term random can refer to a weighted random distribution at one or more positions, or all positions of a polynucleotide, where degeneracy is not equally distributed among the four standard nucleotides at each position defined as random. In some embodiments, the term random can refer to a biased distribution of the four standard nucleotides at one or more positions. Random polynucleotides can also be understood to include one or more base analogues as part of the nucleotides available for distribution at the one or more positions. Thus, in some embodiments, the plurality of random primers can be entirely random at each position of the primer. In some embodiments, the random sequence of a random primer can include interspersed positions having a fixed nucleotide or regions having a fixed sequence of two or more nucleotides, if desired.

In certain embodiments the overall base composition of the primer mixture can be selected, for example to optimize amplification across the sample nucleic acids. In some embodiments, the primer mix comprises a balanced mixture having approximately 50% AT/GC distribution. In other embodiments, the primer mix comprises a mixture that is AT-rich. Any number of primer mixtures, or combinations thereof, can be used in the methods provided herein, and composition of balanced and AT-rich primer mixtures are further described in the incorporated materials of WO 2014/018093.

In certain embodiments the length of the primers in the primer mixture can be selected to optimize amplification across the sample nucleic acids. In certain other embodiments, the set of random amplification primers are about 3, 4, 5, 6, 7, 8, 9, 10, 11, 12, 13, 14, 15, 16, 17, 18, 19, 20, 21, 22, 23, 24 , 25, 26, 27, 28, 29 or greater than about 30 nucleotides in length, or a combination thereof. It will be appreciated that the exact length, composition of each base in a mixture of n-mers can be adjusted as needed to generate a desired level of amplification uniformity across a nucleic acid target such as genomic DNA, as described in the incorporated materials of WO 2014/018093. As a specific example, the method can utilize a balanced (AT/GC) mix of 9-mer random primers for amplification of ssDNA.

In certain embodiments, the double stranded DNA can be further treated to remove single strand overhangs to form blunt ended DNA, thereby preparing a nucleic acid library. In some embodiments, the method can further comprise a DNA repair step comprising contacting the nucleic acids with an enzyme selected from the group consisting of Uracil N-Glycosylase (UNG), Uracil DNA Glycosylase (UDG), Endonuclease IV, Endonuclease VIII, formamidopyrimidine-DNA glycosylase (FPG), DNA-(apurinic or apyrimidinic site) lyase, and Pol β. In some embodiments, the DNA repair step is performed prior to the primer extension step. In some embodiments, the DNA repair step is performed after primer extension step. In some embodiments, the DNA repair step is performed prior to removal of overhangs. In some embodiments, the DNA repair step is performed after removal of overhangs.

One example of such methods is set forth in greater detail below in Example 2. In one exemplary embodiment for library preparation from ssDNA, the method can comprise the following steps. DNA repair is performed, comprising excision of uracil using a uracil DNA excision mix (UDEM). Next, all DNA is converted to ssDNA by denaturation. Random primers are added and end repair is performed to extend the primers and generate blunt-ended fragments for ligation. The end repair reaction can be performed, for example, using a DNA polymerase, such as, for example, T4 DNA polymerase is utilized. The end repair reaction can also further comprise a polynucleotide kinase, such as, for example, T4 polynucleotide kinase. In some embodiments, the polymerase and kinase reactions are combined, and the reaction mixture contains dNTPs and ATP. Size selection can then be performed. In some embodiments, a beads to DNA ratio of 1.2 to 1 is used, but can be varied depending on sample quality and downstream applications. The method can further comprise an A-tailing step, followed by ligation of adapters having a 3' T overhang. An optional clean up step can be performed to remove adapter dimers and unligated fragments. The ligated DNA fragments can optionally be enriched by PCR to amplify fragments with adapters on both ends. This example is only one of a variety of ways to perform the methods described herein.

Methods of Sequencing Nucleic Acids

Some of the methods and compositions provided herein include sequencing a nucleic acid library. A number of DNA sequencing techniques are known in the art, including fluorescence-based sequencing methodologies (See, e.g., Birren et al., Genome Analysis Analyzing DNA, 1, Cold Spring Harbor, N.Y.). In some embodiments, automated sequencing techniques understood in that art are utilized. In some embodiments, parallel sequencing of partitioned amplicons can be utilized (PCT Publication No WO2006084132). In some embodiments, DNA sequencing is achieved by parallel oligonucleotide extension (See, e.g., U.S. Pat. Nos. 5,750, 341; 6,306,597). Additional examples of sequencing techniques include the Church polony technology (Mitra et al., 2003, Analytical Biochemistry 320, 55-65; Shendure et al., 2005 Science 309, 1728- 1732; U.S. Pat. Nos. 6,432,360, 6,485,944, 6,511,803), the 454 picotiter pyrosequencing technology (Margulies et al., 2005 Nature 437, 376-380; US 20050130173), the Solexa single base addition technology (Bennett et al., 2005, Pharmacogenomics, 6, 373-382; U.S. Pat. Nos. 6,787,308; 6,833,246), the Lynx massively parallel signature sequencing technology (Brenner et al. (2000). Nat. Biotechnol. 18:630-634; U.S. Pat. No. 5,695,934; 5,714, 330), and the Adessi PCR colony technology (Adessi et al. (2000). Nucleic Acid Res. 28, E87; WO 00018957).

Next- generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al, Nature Rev. Microbiol, 7- 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos Biosciences, and emerging platforms commercialized by VisiGen, Oxford Nanopore Technologies Ltd., Life Technologies/Ion Torrent, and Pacific Biosciences, respectively.

In pyrosequencing (U.S. Pat. Nos. 6,210,891; 6,258,568), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al, Clinical Chem., 55-641-658, 2009; MacLean et al, Nature Rev. Microbiol, 7' 287-296; U.S. Pat. Nos. 6,833,246; 7,115,400; 6,969,488), sequencing data are produced in the form of shorter-length reads. In this method, single-stranded fragmented DNA is end-repaired to generate 5'-phosphorylated blunt ends, followed by Klenow- mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al, Clinical Chem., 55-641-658, 2009; U.S. Pat. Nos. 5,912,148; 6,130,073) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run. In certain embodiments, nanopore sequencing is employed (see, e.g., Astier et al., J. Am. Chem. Soc. 2006 Feb. 8; 128(5):1705-10). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

EXAMPLES

Example 1—Library Oreparation from a FFPE DNA Sample

The amount of DNA obtained from a FFPE sample that is used in the preparation of a nucleic acid can be adjusted according to the level of degradation of the FFPE DNA. Any known method can be used to determine the level of degradation, such as, use of an Agilent 2100 Bioanalyzer, or qPCR. The level of fragmentation was used to determine if selective shearing was required. Selective shearing was performed on samples of low quality DNA in order to avoid shorter fragments becoming even shorter after shearing. Samples containing lower levels of fragmentation were sheared without removing the shorter fragments.

Selective Shearing

Selective shearing was performed on samples of low quality DNA in order to avoid shorter fragments becoming even shorter after shearing. Larger DNA strands in the FFPE sample were fragmented by selective shearing. Depending on the level of degradation of the FFPE DNA, from 100 ng to about 1 µg FFPE DNA was added to resuspension buffer (RSB; TruSeq DNA Sample Prep Kit, Illumina, Inc.) to a total volume of 12.5 µl. A Bead Mix was made by diluting AMPURE XP beads 1:1 (v/v) in water, and 20 µl of the Bead Mix was added to the FFPE DNA. The sample was then incubated for 5 minutes at room temperature. The beads were magnetically captured and 30 µl of the supernatant (S1) containing unbound, shorter DNA fragments (<550 bp) was removed and stored for later use. The captured beads, containing fragments >550 bp were resuspended in 50 µl RSB, incubated for 5 minutes at room temperature and the beads were magnetically captured. The supernatant (S2) was transferred to a COVARIS sonication tube and shearing was performed using settings optimized to fragment DNA with median insert size of 350 bp, with 45 seconds at duty cycle: 10%; intensity 5; bursts/second: 200; and mode-frequency: sweeping. These settings vary depending on the Covaris platform used. The shearing conditions were optimized in the Covaris S2 that seem to damage less the DNA during the fragmentation process: duration 110 seconds, duty cycle: 5%; intensity 5; burst/second: 200 and mode frequency: sweeping. The sheared sample (S2; 50 µl) was combined with the supernatant S1 (30 µl) for subsequent steps.

The combined supernatant was added to 118 µl beads in order to capture all DNA fragments in the beads. The solution was then incubated at room temperature for 5 minutes and the beads were magnetically captured. The supernatant was removed and discarded, the beads were washed with 200 µl 80% ethanol, incubated, and repeat washed discarding all wash supernatants. The beads were dried at room temperature, resuspended, incubated for 2 minutes at room temperature, magnetically cleared and the supernatant transferred to the final sample tube or plate well, which contained DNA fragments of the FFPE original sample with the desired fragment size distribution. In the foregoing, the ratio of beads: DNA can be optimized to obtain different insert sizes depending on the application.

Optional DNA Repair

Following selective shearing of the FFPE sample DNA, the DNA was repaired. The DNA was repaired using a PreCR Repair Mix (NEB), which includes an enzyme cocktail for repairing damaged nicked DNA prior to amplification processes. The solution was mixed well, sealed with a Microseal "B" adhesive seal and incubated at 37° C. for 20 minutes. AMPURE XP beads were added to the wells at a 1.6:1 (v:v) beads: DNA ratio, mixed and the plate incubated at room temperature for 5 minutes. The beads were then magnetically captured until the liquid turns clear. The supernatant was discarded and the beads were washed twice with 80% ethanol. The beads were dried, then resuspended in 42 µl RSB and, incubated for 2 minutes at room temperature. The supernatant containing 40 µl repaired DNA was retrieved for subsequent steps. The sheared and repaired DNA may be stored at −20° C. for up to 7 days before proceeding with the library protocol.

An alternative DNA repair method included the use of the Epicentre's Uracil-DNA Excision mix (UDEM), which contained two enzymes, HK™-UNG (Heat-Killable Uracil N-Glycosylase [UNG]) and Endonuclease IV with or without FPG. HK-UNG cleaves the uracil base from a uracil-deoxynucleotide in any DNA, creating an abasic site at the location of dUTP incorporation. Endonuclease IV then cleaves the phosphodiester bond at this abasic site generating a series of digestion fragments. Fpg (formamidopyrimidine [fapy]-DNA glycosylase) (also known as 8-oxoguanine DNA glycosylase) acts both as a N-glycosylase and an AP-lyase. The N-glycosylase activity releases damaged purines from double stranded DNA, generating an apurinic (AP site). The AP-lyase activity cleaves both 3' and 5' to the AP site thereby removing the AP site and leaving a 1 base gap. DNA repair using UDEM was performed according to the description in Example 2 below.

An alternative DNA repair method included the use of USER treatment with or without FPG. USER Enzyme (New England Biolabs) includes a mixture of Uracil DNA glycosylase (UDG) and Endonuclease VIII. UDG catalyzes the excision of a uracil base, forming an abasic (apyrimidinic) site while leaving the phosphodiester backbone intact. The activity of Endonuclease VIII breaks the phosphodiester backbone at the 3' and 5' sides of the abasic site so that base-free deoxyribose is released. FPG (formamidopyrimidine [fapy]-DNA glycosylase) (also known as 8-oxoguanine DNA glycosylase) (Epicentre) acts both as a N-glycosylase and an AP-lyase. The N-glycosylase activity releases damaged purines from double stranded DNA, generating an apurinic (AP site). The AP-lyase activity cleaves both 3' and 5' to the AP site thereby removing the AP site and leaving a 1 base gap. To 70 µl of selective sheared DNA, was add 10 µl of ThermoPoi® Reaction Buffer (10×) (NEB), 10 µl of USER (1 U/µl) and 10 µl FPG (8 U/µl). The solution was mixed well, sealed with a Microseal "B" adhesive seal and incubated at 37° C. for 30 minutes. AMPURE XP beads were added to the wells at a 1.6:1 (v:v) beads: DNA ratio, mixed and the plate incubated at room temperature for 5 minutes. The beads were magnetically captured until the liquid turns clear. The supernatant was discarded and the beads are washed twice with 80% ethanol. The beads were dried, then resuspended in 42 µl RSB and, incubated for 2 minutes at room temperature. The supernatant containing 40 µl of repaired DNA is then retrieved for subsequent steps. The sheared and repaired DNA may be stored at −20° C. for up to 7 days before proceeding with the library protocol.

Rec J Exonuclease Treatment

Following FFPE sample shearing, and before or after optional DNA repair step, removal of ssDNA and of ssDNA overhangs was performed, using RecJ exonuclease treatment. To 40 µl of the sample DNA, 5 µl 10× RecJ Exonuclease Reaction Buffer and, 5 µl RecJ exonuclease (10 U/µl) were added and the sample was incubated at 37° C. for 30 minutes followed by the addition of 5 µl EDTA (0.5 M) to inactivate the RecJ exonuclease. AMPURE XP beads were added to the solution in a ratio 1.6:1 (v:v) beads: DNA, mixed and incubated for 5 minutes at room temperature, followed by bead capture until the solution clears. The supernatant was removed, discarded and the beads were washed twice with 80% ethanol. The beads were dried, resuspended in 62.5 µl RSB, mixed and incubated for 2 minutes at room temperature, captured until the supernatant was clear, and the supernatant transferred to a new tube/plate well. The sample may be stored at −15° C. to −25° C. prior to continuing on with library preparation.

End Repair and Size Selection

Repair of the fragmented ssDNA ends was performed by adding 40 µl of End Repair Mix buffer to the captured Rec J treated sample supernatant (60 µl). The solution was mixed and incubated at 30° C. for 30 minutes. A protocol for size selection was selected according to the quality of the FFPE sample. For a high quality FFPE sample, a double size selection to target 350 bp median insert size was performed (See e.g., TruSeq Nano DNA Sample Prep Guide, Illumina, San Diego). In order to remove the larger fragments, a diluted bead mixture was prepared by mixing 95 µl beads with 65 µl of PCR grade water per sample. One-hundred and sixty microliters of diluted AMPURE XP beads were added to 100 µl of end-repaired sample. After mixing, the solution was incubated 5 minutes incubation at room temperature. The solution was magnetically cleared and the supernatant containing fragments <550 bp was transferred (not discarded) to a new tube/plate well. In order to remove the small DNA fragments (<120 bp), 30 µl of undiluted beads were added to the 250 µl of supernatant. The solution was incubated for 5 minutes at room temperature and magnetically cleared. This supernatant was discarded and, the beads were rinsed twice with 80% ethanol, then dried. The dried bead pellet was resuspended in 20 µl RSB, the beads were magnetically captured and the supernatant (17.5 µl) was transferred to a new 0.3 ml Eppendorf tube/plate well. Once the ends of the fragmented ssDNA were repaired they are adenylated. The sample may be stored at −15° C. to −25° C. prior to continuing on with library preparation.

Adenylation and Adapter Ligation

Once the ends of the damaged DNA are repaired, they were adenylated and adapter ligated for further processing of the library. To the 17.5 µl of end-repaired DNA fragments, 12.5 µl of A-tailing mix was added (See e.g., TruSeq Nano DNA Sample Prep Guide, Illumina, San Diego). The sample was mixed and incubated at 37° C. for 30 minutes followed by a heat-inactivation at 70° C. for 5 minutes and cool down at 4° C. for 5 minutes. To the adenylation reaction, 2.5 µl RSB, 2.5 µl Ligase Mix and 2.5 µl of adapters were added. The ligation mixture was incubated at 30° C. for 10 minutes and the reaction stopped by addition of 5 µl Stop Ligation buffer. AMPURE XP beads were added to the ligated DNA fragments in a 1:1 (v:v) ratio, followed by room temperature incubation for 5 minutes. The beads were magnetically captured, washed twice with 80% ethanol, and dried as previously described. The dried beads were resuspended in 52.5 µl RSB, incubated at room temperature for 2 minutes, and captured magnetically with transfer of supernatant to a new 1.7 ml Eppendorf tube/plate well. Another round of AMPURE XP bead capture with a ratio of 1:1 (v:v) was undertaken, however 27.5 µl of RSB was added to the dried beads, the beads were magnetically captured and 25 µl of clear supernatant was transferred to a PCR well plate. Following adapter ligation, the adapter ligated DNA were quantitated by qPCR. Primers specific to the ligated adapters can be used in a PCR reaction if amplification is desired.

Example 2—Preparation of ssDNA by Random Primer Extension and End Repair

This example illustrates the preparation of a substrate for nucleic acid sequencing from nucleic acids obtained from a FFPE sample. First, DNA from a FFPE sample was quantitated and sheared. Briefly, DNA was quantitated using a fluorometric quantification system. Example systems include the Qubit, QuantiFluor, and Picogreen systems. Quantitated DNA was resuspended to 10 ng/μl in 52.5 μl, and then sheared in a Covaris tube using TruSeq Nano v2 350 bp shearing conditions with a duty cycle protocol (intensity: 5.0%; 200 bursts/sec; duration: 110 sec; mode: frequency sweeping; and temperature: 7° C.). Sheared DNA was captured by transferring a 50 μl aliquot of the sheared sample to a sample plate well, adding 80 μl of AMPure XP beads (SPB beads). The sample well was sealed, agitated at 1800 rpm for 2 minutes, incubated at room temperature for 3 minutes, and spun at 280 g for 1 minute. The beads were captured on a magnetic stand for 5 minutes, and 125 μl supernatant was discarded. The beads were washed twice in 200 μl 80% ETOH, and air dried for 5 minutes. The captured DNA was eluted from the beads by adding 82.5 μl RSB, sealing the sample well, agitating the beads at 1800 rpm for 2 minutes, incubating at room temperature for 2 minutes, spinning the beads at 280 g for 1 min, and performing magnetic capture of the beads for 5 minutes. An 80 μl aliquot of the eluted DNA sample was transferred to a clean sample plate well.

DNA repair was performed on the sheared DNA. Briefly, a Uracil DNA Excision Mix "UDEM" (Epicentre Technologies) was used to end repair the sheared DNA. A reaction volume was prepared in the sample well that included 10 μl 10× uracil excision mix buffer, 10 μl UDEM, and 80 μl sheared DNA. The sample well was sealed, agitated at 1800 rpm for 1 minute, spun at 280 g for 1 minute, incubated at 37° C. for 30 minutes, and then the reaction stopped by adding 5 μl 0.5 M EDTA. A volume of 168 μl SPB was added to the reaction volume. The beads were washed and air-dried. A volume of 17.5 μl RSB was added to the beads, the sample was agitated and the DNA was eluted. An aliquot of 15 μl eluted end-repaired sample was transferred to a new sample plate well.

The repaired DNA sample was extended. Briefly, an initial reaction volume included 15 μl DNA sample, 5 μl of 1 mM Infinium Balanced 9-mer Randomer (P/N 11246567 Illumina, Inc.). The reaction volume was sealed in the sample plate well, agitated at 1200 rpm for 1 minute, and briefly spun at 280 g, incubated at 98° C. for 5 minutes, then chilled on ice for 5 minutes. To the initial reaction volume 20 μl End Repair Mix, and 10 μl RSB were added. The reaction volume was sealed in the sample plate well, briefly spun at 280 g, and incubated for 30 minutes at 30° C.

Extended DNA was size-selected. To the reaction volume, 50 μl SPB was added. The reaction volume was sealed in the sample plate well, agitated and spun. The magnetic beads were captured, 95 μl supernatant was discarded, and the beads were washed twice and air dried for 5 minutes. Following air drying, 20 μl RSB was added and the beads were agitated, incubated for 5 minutes, and captured for 5 minutes on the magnetic stand. An aliquot of 17.5 μl eluted sample was transferred to a new sample plate well for A-tailing.

The size-selected DNA was A-tailed. Briefly, a reaction volume of 17.5 μl sample, 12.5 μl of A Tailing and Ligation Mix was prepared, the well was sealed, agitated, quick spun and incubated at 37° C. for 30 minutes. The sample was then incubated at 70° C. for minutes and then placed on ice. To the sample, 2.5 μl RSB, 2.5 μl ligase and 2.5 μl adaptor were added, the well was sealed, agitated, quick spun and incubated at 30° C. for ten minutes. Following incubation, 5 μl stop ligation buffer was added to the reaction volume and the well was sealed, agitated, quick spun, then 42.5 μl of SPB beads were added to the reaction volume. The reaction volume was incubated at room temperature for 5 minutes, washed twice and air dried for 5 minutes. Once dried, 52.5 μl RSB was added to the reaction volume, the well was sealed, agitated as incubated, and 50 μl of the reaction volume was transferred to a new sample plate well. The sample was captured with beads and washed, 27.5 μl RSB was added to elute the DNA from the beads and 25 μl sample supernatant was transferred to a well in a PCR plate.

The size-selected DNA was amplified by PCR. Briefly, the reaction volume included: 25 μl sample supernatant, 5 μl PCR primer cocktail mix, 20 μl enhance PCR mix, to a total volume of 50 μl. The reaction volume was agitated and the PCR TruSeq™ Nano program was run for 8 cycles (95° C. for 3 minutes and the following program was performed for 8 cycles: 98° C. for 20 sec, 60° C. for 15 sec, 72° C. for 30 sec, 72° C. for 5 min, and hold at 4° C. until further processing or stored at −20° C.). Following amplification, the sample was spun down and the entire contents (50 μl) were transferred to a well in another plate (e.g., a MIDI plate). SPB beads (50 μl) were added to the sample and the sample well was sealed, agitated and quick spun, the beads were captured and washed. Following air drying of the sample, 32.5 μl RSB was added to the sample to elute the DNA and 30 μl supernatant was transferred to a new sample plate well. The sample library DNA was quantitated using a fluorometric quantification system, or by quantitative PCR. Following quantitation the library was sequenced.

Sequencing results with nucleic acids prepared by the foregoing method were comparable to results obtained when using the dsDNA sample preparation of Example 1.

Example 3—Comparative Analysis

This example describes a comparison of three library preparation methods to determine the effect of including DNA repair and ssDNA removal. Aggressive extraction methods, such as those used to extract DNA from FFPE, can result in the presence of ssDNA. The presence of ssDNA makes a fragment inaccessible to double-stranded adapter ligation. In addition, ssDNA can hybridize to itself (see FIG. 2) or to other ssDNA from a different genomic location, resulting in the formation of chimeras, as shown in FIG. 8. Chimeric pairs are aligned within a normal fragment length of each other, resulting in misalignment and causing false positive single nucleotide variants (SNV).

An example is illustrated in FIG. 8. A large portion of the human genome (approximately 6%) is L1P long interspersed elements (LINEs), which are 97% identical. In a fragmented pool of ssDNA, similar L1P elements from different genomic locations may hybridize. Without exonuclease treatment, such as treatment with Rec J, a chimeric dsDNA fragment will be formed during end repair extension. However, with Rec J treatment, ssDNA is degraded producing short dsDNA fragments. During alignment after paired end sequencing, the Rec J treated fragments are aligned as overlapping reads. However, fragments which are not Rec J treated are aligned within a normal fragment length of each other.

A method performed according to the methods described herein (workflow "A") was compared with two commercially available library preparation methods: 1) KAPA hyper prep kit (Kapa Biosystems, Inc.), and 2) Accel-NGS™ 2S DNA Library Kit (Swift Biosciences, Inc.). For each workflow, 500 ng of medium quality sample DNA was used as input in all three workflows. The KAPA and Swift workflows were performed according to manufacturer's instructions, which do not include DNA repair and ssDNA excision as set forth herein. In contrast, to the KAPA and Swift workflows, workflow "A" comprises UDEM DNA repair followed by Rec J ssDNA degradation. The UDEM repair and RecJ steps were performed as described above in Example 1. Libraries prepared by each of the three workflows were then sequenced on an Illumina HiSeq 2500 instrument according to manufacturer's instructions. Sequencing data was analyzed to calculate percent chimeric pairs, which is the percent of aligned pairs where the reads align to different chromosomes. Sequencing data was also analyzed to calculate percent aligned, which is the percent of reads passing filter that are aligned. Sequencing data was also analyzed to calculate error rate HiQ, which is the percent of high quality bases in reads with a high mapping score that are different to the reference (this calculation inherently includes SNPs, so is always greater than zero).

As shown in FIG. 9, libraries prepared with DNA repair (UDEM treatment) and ssDNA excision (Rec J treatment) resulted in significant decreases in % chimeric pairs, % error rates, and in a significant increase in the % of aligned fragments, compared to the two other workflows.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for preparing a nucleic acid library comprising:
   (a) separating the plurality of nucleic acids into a first fraction of nucleic acids having an average length longer than 550 base pairs, and a second fraction of nucleic acids having an average length shorter than 550 base pairs;
   (b) shearing the nucleic acids of the first fraction under conditions to generate sheared nucleic acids having an average length of 350 base pairs;
   (c) repeating steps (a) and (b); and
   (e) combining the sheared first fraction and the second fraction to obtain a nucleic acid library comprising a combined fraction of polynucleotides.

2. The method of claim 1, further comprising ligating adaptors to ends of the combined fraction of polynucleotides.

3. The method of claim 1, further comprising sequencing the combined fraction of polynucleotides.

4. The method of claim 1, wherein (a) comprises removing single-stranded nucleic acids from the combined fraction of polynucleotides.

5. The method of claim 4, wherein the removing comprises contacting the single-stranded nucleic acids with a single-strand exonuclease.

6. The method of claim 5, wherein the single-strand exonuclease is selected from the group consisting of: RecJ, exonuclease I, exonuclease T, exonuclease VII, exonuclease VIII, and mung bean exonuclease.

7. The method of claim 6, wherein the single-strand exonuclease comprises RecJ.

8. The method of claim 1, further comprising repairing the nucleic acids of the combined fraction of polynucleotides.

9. The method of claim 8, wherein the repairing comprises contacting the combined fraction of polynucleotides with a kinase.

10. The method of claim 8, wherein the repairing comprises hybridizing random primers to the combined fraction of polynucleotides and extending the random primers.

11. The method of claim 8, wherein the repairing comprises contacting the combined fraction of polynucleotides with an enzyme selected from the group consisting of uracil N-glycosylase (UNG), uracil DNA glycosylase (UDG), endonuclease IV, endonuclease VIII, formamidopyrimidine-DNA glycosylase (FPG).

12. The method of claim 11, wherein the repairing comprises contacting the combined fraction of polynucleotides with the UNG and the endonuclease IV.

13. The method of claim 12, wherein the repairing is performed in the absence of the FPG.

14. The method of claim 1, wherein (a) comprises contacting the plurality of nucleic acids with a matrix under conditions wherein nucleic acids greater than about 550 bp selectively bind to the matrix.

15. The method of claim 14, wherein the matrix comprises a plurality of beads.

16. The method of claim 15, wherein the plurality of beads are magnetic beads.

17. The method of claim 1, wherein the (b) comprises sonicating the nucleic acids of the first fraction.

18. The method of claim 1, wherein the plurality of nucleic acids comprises a fixed sample of nucleic acids.

19. The method of claim 1, wherein the plurality of nucleic acids comprises DNA.

* * * * *